United States Patent
Minneman et al.

(10) Patent No.: US 9,404,729 B1
(45) Date of Patent: Aug. 2, 2016

(54) SYSTEM AND METHOD FOR CHARACTERIZING AND CORRECTING THE OPTICAL RESPONSE OF AN OPTICAL COHERENCE TOMOGRAPHY SYSTEM

(71) Applicant: Insight Photonic Solutions, Inc., Lafayette, CO (US)

(72) Inventors: Michael Minneman, Lafayette, CO (US); Paul Boschert, Lafayette, CO (US); Michael Crawford, Lafayette, CO (US); Jason Ensher, Lafayette, CO (US)

(73) Assignee: Insight Photonic Solutions, Inc., Lafayette, CO (US)

( * ) Notice: Subject to any disclaimer, the term of this patent is extended or adjusted under 35 U.S.C. 154(b) by 45 days.

(21) Appl. No.: 14/190,774

(22) Filed: Feb. 26, 2014

Related U.S. Application Data

(60) Provisional application No. 61/769,848, filed on Feb. 27, 2013.

(51) Int. Cl.
*G01B 9/02* (2006.01)
*A61B 3/10* (2006.01)

(52) U.S. Cl.
CPC ............ *G01B 9/02091* (2013.01); *A61B 3/102* (2013.01); *G01B 9/02002* (2013.01); *G01B 9/02072* (2013.04); *G01B 9/02083* (2013.01)

(58) Field of Classification Search
CPC .......... G01B 9/02091; G01B 9/02004; G01B 9/02002; G01B 9/02044; G01B 9/02083; G01B 9/0209; G01B 9/0207; G01B 9/02072; G01B 9/02075; A61B 3/102; A61B 5/0033; A61B 5/0073; A61B 5/0066
See application file for complete search history.

(56) References Cited

U.S. PATENT DOCUMENTS

| | | | | |
|---|---|---|---|---|
| 4,293,222 A | * | 10/1981 | Caruso et al. | 356/319 |
| 2006/0114462 A1 | * | 6/2006 | Zhou et al. | 356/425 |
| 2007/0276269 A1 | * | 11/2007 | Yun et al. | 600/504 |
| 2008/0198367 A1 | * | 8/2008 | Chang et al. | 356/73 |
| 2014/0125988 A1 | * | 5/2014 | Wang | A61B 3/102 356/479 |
| 2014/0307753 A1 | * | 10/2014 | Minneman | H01S 5/06256 372/20 |

OTHER PUBLICATIONS

Dennis Derickson, SGDBR singl-chip wavelength tunable lasers for swept source OCT, Jan. 19, 2008, SPIE 6847, pp. 1-2.*

* cited by examiner

*Primary Examiner* — Michael P Lapage
(74) *Attorney, Agent, or Firm* — Renner, Otto, Boisselle and Sklar, LLP

(57) ABSTRACT

A system and method for correcting the optical response of an OCT system is presented. The system and method characterize the optical response of the OCT system to determine an optical loss of the OCT system as a function of wavelength. The optical loss corresponds to a reduction in the magnitude of electromagnetic radiation leaving an interferometer of the OCT system compared to the electromagnetic radiation entering the interferometer. The optical loss of the OCT system may be determined by generating output signals using the OCT system when the system does not contain a sample or contains an electromagnetic radiation absorbing material. A controller may control the source to pre-emphasize the electromagnetic radiation to correct for the optical response of the OCT system.

10 Claims, 3 Drawing Sheets

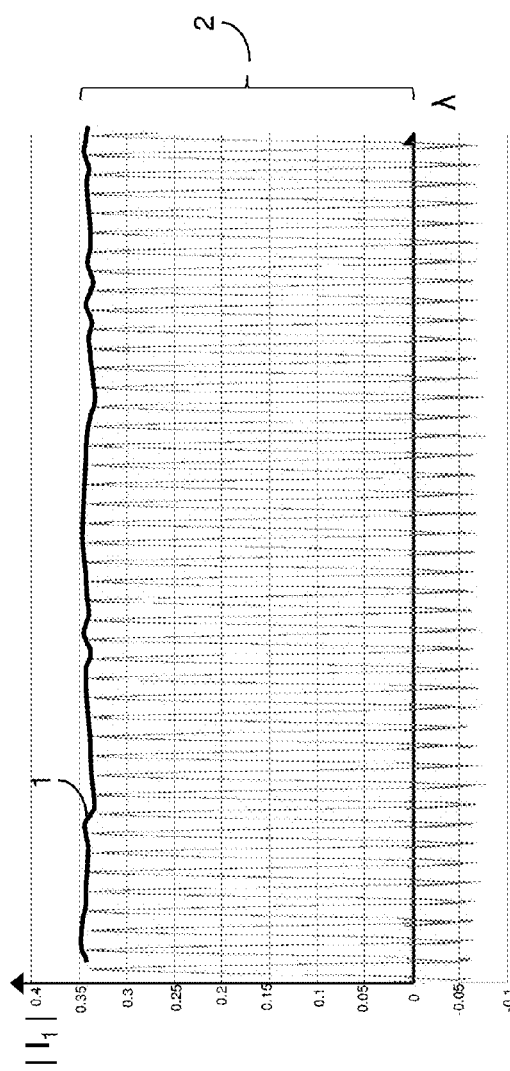
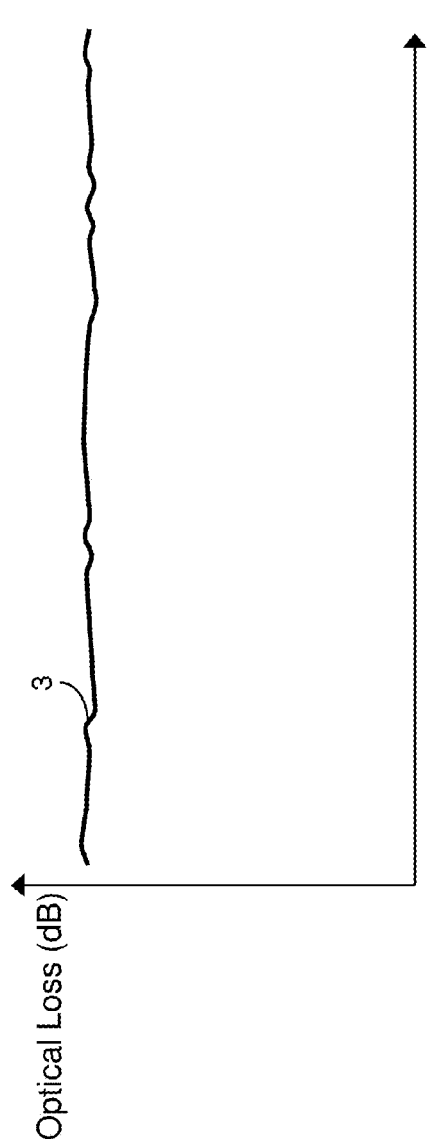
FIG. 1A
FIG. 1B

SYSTEM AND METHOD FOR CHARACTERIZING AND CORRECTING THE OPTICAL RESPONSE OF AN OPTICAL COHERENCE TOMOGRAPHY SYSTEM

RELATED APPLICATION

This application is a Non-Provisional of U.S. Application No. 61/769,848 filed Feb. 27 2013, which is herein incorporated by reference in its entirety.

TECHNICAL FIELD

The present invention relates generally to a system and method to improve optical coherence tomography (OCT) image quality by characterizing the optical response of an OCT system and pre-emphasizing the optical signal from the OCT system to minimize the impact of wavelength-periodic optical system losses.

BACKGROUND

In optical coherence tomography (OCT), to generate an image of the structure of a sample (e.g., a biological tissue), electromagnetic radiation is directed by the OCT system at the sample. Variations in the radiation that is reflected from the sample indicate structure in the sample. Ideally, to reduce artifacts in OCT images of the sample, the electromagnetic radiation directed at the sample by the OCT system should have a flat structure, without periodic variations in intensity. That is, ideally the magnitude of the electromagnetic radiation directed at the sample should not vary with wavelength. However, the OCT system can generate periodic variations in the intensity of the electromagnetic radiation, reducing image quality and introducing artifacts into OCT images.

In OCT, electromagnetic radiation is split, using an interferometer, into a reference path and an imaging path. The electromagnetic radiation returning from the reference path and imaging path are combined in the interferometer into a response signal. In OCT, structure (e.g., tissue layer contrast) is indicated by frequency variation of the response signal. However, the OCT system itself may introduce frequency components into the response signal. The frequency components introduced into the response signal may be incorrectly interpreted as structure (e.g., tissue layers) of the sample.

SUMMARY

The present invention provides a method for correcting the optical response of an OCT system by characterizing the optical response of the OCT system to determine an optical loss of the OCT system as a function of wavelength and pre-emphasizing the electromagnetic radiation generated by the OCT system or processing output signals with the optical loss to correct for the optical response of the OCT system.

According to one aspect of the disclosure, there is provided a method for correcting an optical response of an OCT system. The method includes characterizing the optical response of the OCT system. Characterizing the optical response includes generating electromagnetic radiation through a range of wavelengths and splitting the electromagnetic radiation through a reference path and a sample path, where a sample does not lie in the sample path. Characterizing the optical response also includes detecting the electromagnetic radiation returned from the reference path and the sample path, generating an output signal corresponding to the received electromagnetic radiation, and processing the output signals to determine an optical loss of the OCT system as a function of wavelength of the electromagnetic radiation. The method also includes pre-emphasizing, in relation to the optical loss, and generating the electromagnetic radiation through the range of wavelengths.

Alternatively or additionally, determining the optical loss includes calculating a correction signal such that, when the generated electromagnetic radiation is pre-emphasized according to the correction signal and split through the reference path and the sample path, the detected electromagnetic radiation does not contain periodic variation in magnitude.

Alternatively or additionally, the method includes splitting the electromagnetic radiation through the reference path and the sample path (where the sample lies in the sample path), detecting electromagnetic radiation returned from the reference path and the sample path (where the detector generates output signals corresponding to the received electromagnetic radiation), and processing the output signals to generate an image.

Alternatively or additionally, generating the electromagnetic radiation when characterizing the optical response includes generating the electromagnetic radiation such that an intensity of the electromagnetic radiation is approximately constant across the range of wavelengths.

Alternatively or additionally, a proxy reflector is inserted into the sample path such that electromagnetic radiation split through the sample path reflects off of the proxy reflector and generates a fringe signal, the fringe signal comprising electromagnetic radiation returning from the sample path. Determining the optical loss comprises measuring an amplitude envelope of the output signal and calculating a correction signal from the amplitude envelope such that, when the generated electromagnetic radiation is pre-emphasized according to the correction signal and split through the reference path and the sample path, the detected electromagnetic radiation does not contain periodic variation in magnitude.

According to another aspect of the disclosure, a system includes an electromagnetic radiation source, an interferometer, a detector, and a controller. The electromagnetic radiation source is operable to generate electromagnetic radiation through a range of wavelengths. The interferometer is coupled to the electromagnetic radiation source. The interferometer includes a reference path and a sample path. The detector receives electromagnetic radiation returned from the reference path and the sample path. The detector generates output signals corresponding to the received electromagnetic radiation. The controller is coupled to the detector and the electromagnetic radiation source. The controller selectively causes electromagnetic radiation to be generated when a sample does not lie in the sample path, processes the output signals to determine an optical loss of the OCT system as a function of wavelength of the electromagnetic radiation, and selectively causes pre-emphasized electromagnetic radiation to be generated. The intensity of the electromagnetic radiation for a given wavelength is related to the optical loss at the given wavelength.

Alternatively or additionally, determining the optical loss includes calculating a correction signal such that, when the generated electromagnetic radiation is pre-emphasized according to the correction signal and split through the reference path and the sample path, the detected electromagnetic radiation does not contain periodic variation in magnitude.

Alternatively or additionally, selectively causing electromagnetic radiation to be generated when a sample does not lie in the sample path includes selectively causing electromagnetic radiation to be generated having an intensity that is approximately constant across the range of wavelengths.

Alternatively or additionally, the optical loss is equal to the output signals.

Alternatively or additionally, the at least one electromagnetic radiation source is a semiconductor tunable laser source.

Alternatively or additionally, the source comprises a semiconductor laser.

Alternatively or additionally, the source is a sample grating distributed Bragg reflector (SG-DBR) laser.

The foregoing and other features of the invention are hereinafter fully described and particularly pointed out in the claims, the following description and annexed drawings setting forth in detail certain illustrative embodiments of the invention, these embodiments being indicative, however, of but a few of the various ways in which the principles of the invention may be employed.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

FIG. 1A is an exemplary output signal of an OCT system prior to correction;

FIG. 1B is an exemplary optical response of the OCT system of FIG. 1A;

DESCRIPTION

Figure 1C:
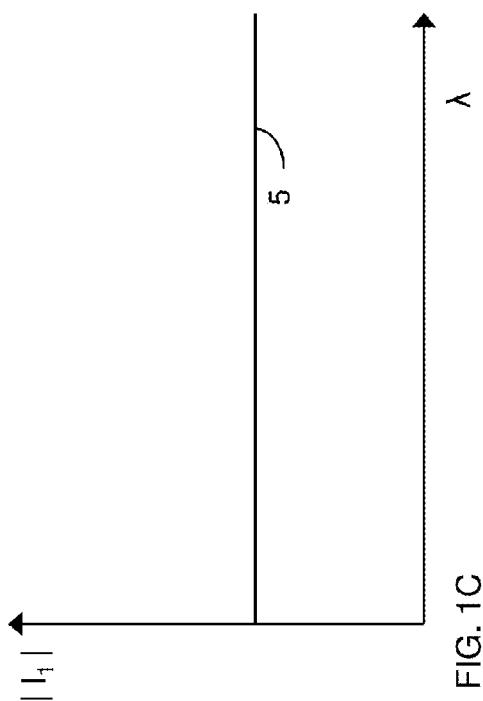
FIG. 1C is an exemplary output signal of the OCT system of FIG. 1A after correction with the optical loss signal of FIG. 1B.

The present invention provides a method for correcting the optical response of an OCT system. The method includes characterizing the optical response of the OCT system to determine an optical loss of the OCT system as a function of wavelength. The method determines the optical loss of the OCT system by generating output signals using the OCT system when the system contains a single reflection. The method corrects for the optical loss by pre-emphasizing the electromagnetic radiation generated by the light source in the OCT system.

Turning to FIG. 1A, an exemplary output signal 1 of an OCT system is shown. The output signal 1 represents the intensity of electromagnetic radiation leaving an interferometer of the OCT system. The output signal 1 of the OCT system is not constant, i.e., the optical signal 1 varies with the wavelength of the electromagnetic radiation. The variations in the amplitude envelope of output signal 1 may introduce image artifacts into images created using the OCT system. Note that the amplitude envelope of output signal 1 represents the wavelength-dependent loss through the OCT system, while the actual signal from a single reflection in the OCT system is a sinusoidally-varying optical signal of relatively high frequency 2. The profile of the output signal 1 represents the variation in the envelope of the varying optical signal of relatively high frequency 2.

Turning to FIG. 1B, the variations in the amplitude envelope of output signal may be caused by the optical response of the OCT system. The optical response of the OCT system may be characterized by an optical loss 3 of the system. The optical loss 3 represents, for each wavelength of electromagnetic radiation generated by a source of the OCT system, the change in magnitude of the generated electromagnetic radiation leaving the source (i.e., an input signal) compared to the magnitude of the electromagnetic radiation leaving the interferometer of the OCT system (i.e., the output signal 1). That is, the optical loss 3 represents the change (e.g., loss of intensity) imposed on an input signal by the OCT system. In FIG. 1B, the optical loss 3 is quantified in decibels (i.e., $10*\log_{10}(I_1/I_0)$ where $I_1$ is the magnitude of the output signal 1 and $I_0$ is the magnitude of the input signal).

As depicted in FIG. 1B, the optical loss 3 of the OCT system may not be constant, i.e., the optical loss 3 may vary with the wavelength of the electromagnetic radiation. The optical loss 3 may decrease (i.e., increase in negative decibels, since 0 dB corresponds to no optical loss) for certain wavelengths of electromagnetic radiation representing a reduction in the magnitude of the output signal relative to the magnitude of the input signal. The variations in the optical loss 3 may introduce image artifacts into images created using the OCT system. For example, if the optical loss 3 varies periodically with optical frequency, the variation may be interpreted as a spurious reflection in an OCT system.

Turning to FIG. 1C, a corrected output signal 5 of the OCT system is depicted.

As will be discussed below, by determining the optical loss 3, it is possible to correct for the optical response of the system. That is, it is possible to pre-emphasize the power spectral profile of the electromagnetic radiation generated by the light source in the OCT system, such that the magnitude of the output signal 1 of the corrected OCT system is approximately constant. By correcting for the optical response of the OCT system, it is possible to remove or significantly reduce the imaging artifacts caused by the optical response of the OCT system. For example, the variation in magnitude between wavelengths of the corrected (i.e., pre-emphasized) electromagnetic radiation may be substantially reduced compared to the variation in magnitude between wavelengths of the uncorrected (i.e., non pre-emphasized) electromagnetic radiation generated by the light source. As will be understood by one of ordinary skill in the art, substantially reduced may signify, e.g., a reduction by greater than 25%, greater than 50%, greater than 75%, greater than 90%, or greater than 95%.

Figure 2:
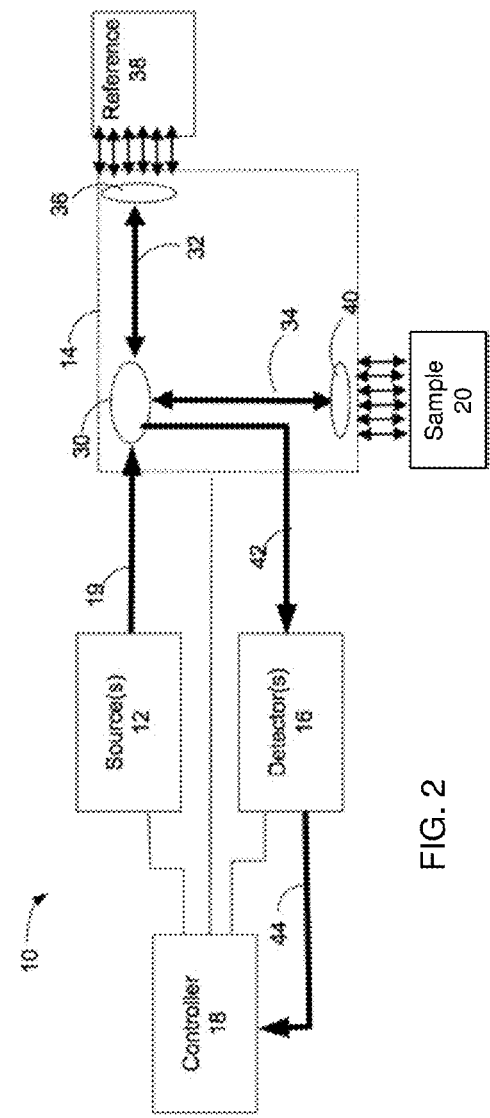
FIG. 2 is a block diagram representing an exemplary OCT system.

An exemplary OCT system 10 in accordance with aspects of the present invention is illustrated in FIG. 2. The OCT system 10 includes at least one electromagnetic radiation source 12, an interferometer 14 (identified by dashed lines), a detector 16 and a controller 18. Electromagnetic radiation 19 is directed from the at least one radiation source 12 to a sample 20 to detect a physical characteristic associated with the sample, as discussed herein.

The at least one electromagnetic radiation source 12 is operable to generate electromagnetic radiation through a range of wavelengths. The electromagnetic radiation source 12 may be an electronically tunable laser configured to electronically tune the output wavelength of the electromagnetic radiation 19. The output wavelength of the source 12 may be electronically-tuned by adjusting one or more input currents to the source 12. In one exemplary illustration, the device may be tuned by changing up to 5 different input currents to the device. By electronic tuning the output wavelength of the emitted electromagnetic radiation 19, the source 12 can be programmed and/or controlled by the controller 18 to output electromagnetic radiation 19 at a desired wavelength having a desired magnitude (i.e., intensity). The source 12 may be controlled to sweep the output wavelength across a range of wavelengths and control the magnitude of each wavelength in the range of wavelengths.

The source 12 may be, e.g., a semiconductor laser, a sampled grating distributed Bragg reflector (SG-DBR) laser, a vertical-Cavity Surface-Emitting Laser (VCSEL), a multi-section laser (such as Super-Structure Grating DBR lasers (SSG-DBRs)), a Digital Supermode DBR laser (DS-DBRs), a Y-Branch laser, or any other suitable source of electromagnetic radiation. The source 12 may also comprise multiple sources of electromagnetic radiation.

The interferometer 14 (identified generally by the dashed lines) may be coupled to the electromagnetic radiation source 12 by a coupler 30. Any type of interferometer may be used in accordance with aspects of the present invention. Exemplary interferometers include, for example: a Mach-Zehnder interferometer, a Michelson interferometer, a Fabry-Perot interferometer, etc. The interferometer 14 may include fewer components or more components than identified within the confines of the dashed line. The illustrated interferometer 14 is exemplary and provided to assist one skilled in the art in understanding aspects of the present invention.

Generally, the coupler 30 splits the received electromagnetic radiation into a reference path 32 and a sample path 34. For the reference path 32, the electromagnetic radiation is output through a lens unit 36 and reflected off a reference 38. In one embodiment, the reference 38 may be a mirror or any known reference reflector with partial reflectivity. For the sample path 34, the electromagnetic radiation is output through a lens unit 40 and reflected off a sample 20. The sample 20 may be any desirable sample. Exemplary samples include, for example, human tissue, inanimate objects, etc.

The coupler 30 may be any type of device that may be used to split or route electromagnetic radiation received (e.g., signal 19) into two or more radiation paths (e.g., paths 32, 34) and/or join two or more received radiation paths into a single signal (e.g., output optical signal 42). For example, the coupler may be a splitter for separating and/or combining optical mediums (e.g., a fiber optic cable, etc.), a beam splitter and the like. As shown in FIG. 2, the coupler 30 may be a 3 dB coupler that splits the incoming electromagnetic radiation into two separate radiation paths (e.g., reference path 32 and sample path 34) of approximately equal intensity of electromagnetic radiation. Alternatively, coupler 30 may be a 90/10 coupler that splits the incoming radiation into two separate radiation paths comprising 10% of the radiation coupled to reference path 32 and 90% to sample path 34. The two radiation paths 32 and 34 may be recombined after the electromagnetic radiation has traversed separate radiation paths 32, 34 at the coupler 30 and/or a different coupler (not shown).

The coupler 30 additionally functions to combine the electromagnetic radiation that has traversed radiation paths 32, 34. Radiation returning from the reference path 32 and the sample path 34 travels through the respective lens unit (e.g., 36, 40) and is combined with the coupler 30 or another beam combining component to form an output optical signal 42. The output optical signal 42 is a fringe pattern of magnitude vs. time or spatial dimension that may be detected by a detector 16 (e.g., a photodetector, a phase detector, frequency detector, linear detector array or other suitable detector). One of ordinary skill in the art will readily appreciate that the output optical signal 42 and the detector may 16 vary based on the electromagnetic radiation, wavelength, frequency and/or range used in conjunction with the system. The detector 16 may be a single channel and/or a multi-channel detector.

The detector 16 receives electromagnetic radiation (i.e., the output optical signal 42) returned from the reference path 32 and the sample path 34 (also referred herein as target path). The detector 16 receives the combined, interfered electromagnetic radiation (i.e., the output optical signal 42). The detector 16 generates one or more output signals 44 that are based on the received electromagnetic radiation from the reference path 32 or sample path 34. The output signals 44 are received by controller 18.

The controller 18 processes the output signals 44 to represent data corresponding to magnitude and distance information detected by the detector 16. For example, a graph of reflection magnitude vs. distance may be created for each scan. A single scan of the electromagnetic radiation source produces a one-dimensional graph. The output signals of multiple scans may be combined to generate one or more image signals. For example, multiple scans of one-dimensional graphs are used to assemble a two-dimensional representation of data that relates to the sample, as is conventional. Preferably, the controller 18 processes the output signals 44 to generate image signals from the electromagnetic radiation.

The controller 18 is coupled to the interferometer 14, the detector 16 and the electromagnetic radiation source 12. The controller 18 selectively controls the wavelength of electromagnetic radiation emitted by the source 12 as well as the magnitude of the electromagnetic radiation.

Figure 3:
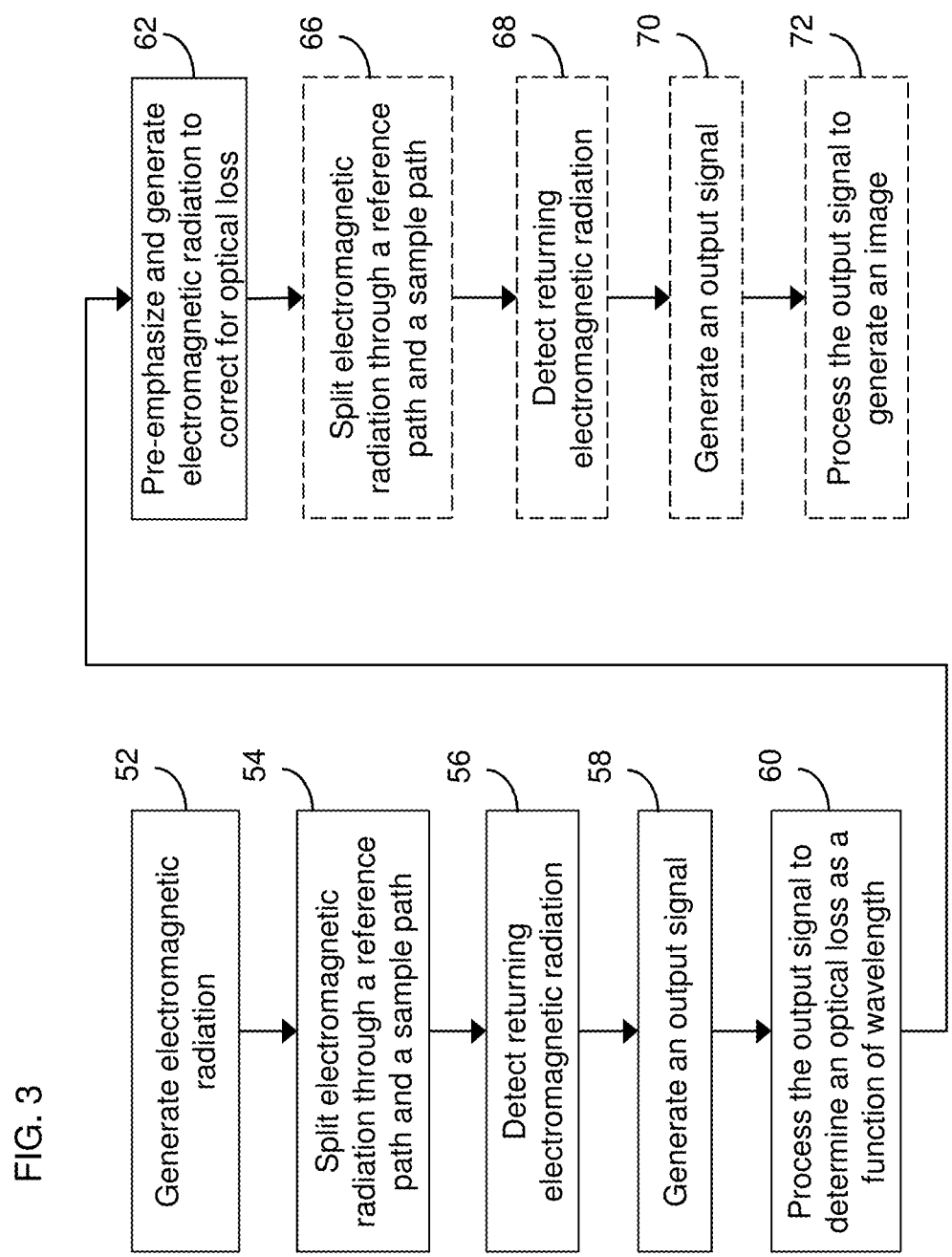
FIG. 3 is a flow diagram illustrating a method for correcting the optical response of an OCT system.

Turning to FIG. 3, a method for correcting the optical response of an OCT system is described. The method steps may be directed and/or performed by the controller 18. In process blocks 52-60, in order to correct the optical response of the OCT system, the method may first characterize the optical response of the OCT system to determine an optical loss as a function of wavelength. In process block 52, the source 12 generates electromagnetic radiation 19. The source 12 may generate electromagnetic radiation 19 across a range of wavelengths with the intensity (i.e., magnitude) of the electromagnetic radiation at each wavelength approximately equal. Alternatively, the source 12 may generate electromagnetic radiation 19 across a range of wavelengths with the different known intensities.

In process block 54, the interferometer 14 splits the electromagnetic radiation 19 through a reference path 32 and a sample path 34. As described previously, the electromagnetic radiation 19 may be split using a coupler 30. In process block 56, the detector 16 detects the output optical signal 42 of the interferometer 14 (i.e., the combined electromagnetic radiation 19 returning from the reference path 32 and the sample path 34). The OCT system 10 may be configured such that, when determining the optical loss, no electromagnetic radiation returns from the sample path 34. For example, an electromagnetic radiation absorbing material may be placed in the sample path 34 such that no electromagnetic radiation returns from the sample path 34. Alternatively, the electromagnetic radiation 19 in the sample path 34 may be directed out of the OCT system 10 such that no electromagnetic radiation returns from the sample path 34. Thus, the output optical signal 42 may comprise only the electromagnetic radiation returning from the reference path 32. As described previously, the combined electromagnetic radiation from reference path 32 and sample path 34 may be a fringe pattern of magnitude vs. time or spatial dimension.

In another aspect of the present invention, the optical loss may be determined with electromagnetic radiation returning from the sample path 34. A proxy reflector may be inserted into sample path 34. The proxy reflector may be a normal element of the calibration of an OCT system, as it is often necessary to use a proxy reflection to match optical path length between reference and sample arms of the interferometer. The combined electromagnetic radiation from the proxy reflector in the sample path 34 and the reference path 32 may be a fringe pattern of magnitude vs. time or spatial dimension. By measuring the amplitudes of the extrema in the fringe pattern of the output signal 44, the amplitude envelope may be determined as illustrated in FIG. 1A, and the effect of the optical loss in the OCT system calculated.

In process block 58, the detector 16 generates an output signal 44 based on the output optical signal 42. In process block 60, the controller 18 processes the output signal 44 to determine the optical loss of the OCT system 10 as a function of wavelength. Processing the output signal 44 to determine the optical loss may comprise, for each wavelength of the electromagnetic radiation 19, subtracting the magnitude of the electromagnetic radiation 19 generated by the source 12 from the magnitude of the output signal 44. For example, the magnitude of the electromagnetic radiation 19 generated by the source 12 may comprise a constant value if the source generated electromagnetic radiation 19 has an approximately equal magnitude for each wavelength of electromagnetic radiation 19. Therefore, when the magnitude of the electromagnetic radiation 19 is constant, the optical loss may be proportional to the output signal 44. For example, the optical loss may be assumed to be equal to the output signal 44 or the optical signal 44 multiplied by a representation of the intensity of the electromagnetic radiation 19 (e.g., the percentage of maximum intensity at which the electromagnetic radiation was generated). Alternatively, the magnitude of the electromagnetic radiation 19 generated by the source 12 may vary by wavelength. In this case, the output signal 44 may be subtracted by a representation of the intensity of the electromagnetic radiation 19 (e.g., the percentage of maximum intensity at which the electromagnetic radiation was generated) or a measurement of the magnitude of the electromagnetic radiation 19. For example, the magnitude of the electromagnetic radiation 19 may be measured prior to entering the interferometer 14. Determining the optical loss may additionally comprise taking the logarithm of the ratio of the magnitude of the output signal and the magnitude of the electromagnetic radiation 19 generated by the source 12.

With further reference to FIG. 3, in process block 62, after determining the optical loss of the OCT system and placing a sample in the sample path 34, the source 12 generates electromagnetic radiation 19 pre-emphasized to correct for optical loss. Pre-emphasizing the electromagnetic radiation may comprise the controller 18 controlling the source 12 such that the magnitude of each wavelength of electromagnetic radiation 19 emitted by the source 12 is set according to the optical loss signal. For example, the current or any other factor the source 12 varies to control the intensity of the generated electromagnetic radiation 19 may be proportional to the optical loss signal. That is, the optical loss signal corresponds to the reduction in intensity of the electromagnetic radiation 19 leaving the interferometer 14 caused by the interferometer 14. Thus, if the optical signal for one wavelength corresponds to a reduction in intensity of 15%, the current supplied to the source 12 when generating the electromagnetic radiation at the given wavelength may be increased by 15%. In this way, the intensity of the electromagnetic radiation at a given wavelength can be corrected to compensate for the reduction in intensity caused by the OCT system (i.e., the optical response). Alternatively, a correction signal to correct the optical response of the system 10 may be calculated from the optical loss. The controller 18 may use the correction signal when correcting the intensity of the electromagnetic radiation 19 created by the source 12. For example, the controller 18 may use the optical loss as an initialization point in determining the control signal. The controller 18 may perform optimization (e.g., nonlinear) to determine a control signal that, when used to pre-emphasize the electromagnetic radiation, results in an output signal 42 that does not vary in intensity with wavelength. As will be understood by one of ordinary skill in the art, an output signal resulting from pre-emphasized electromagnetic radiation that does not vary in intensity with wavelength may comprise a signal where the variations in intensity with wavelength have been substantially reduced compared to an output signal resulting from electromagnetic radiation that was not pre-emphasized. Substantially reduced may signify, e.g., a reduction in variations in intensity with wavelength by greater than 25%, greater than 50%, greater than 75%, greater than 90%, or greater than 95%.

After pre-emphasizing and generating the electromagnetic radiation 19, in optional process block 66, the interferometer 14 splits the electromagnetic radiation 19 through a reference path 32 and a sample path 34. As described previously, the electromagnetic radiation 19 may be split using a coupler 30. In optional process block 66, the detector 16 detects the output optical signal 42 (i.e., the combined electromagnetic radiation 19 returning from the reference path 32 and the sample path 34). As described previously, the output optical signal 42 may be a fringe pattern of magnitude vs. time or spatial dimension. In optional process block 68, the detector 16 generates an output signal 44 based on the output optical signal 42.

Although the invention has been shown and described with respect to a certain illustrated embodiment or embodiments, equivalent alterations and modifications will occur to others skilled in the art upon reading and understanding the specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function (i.e., that is functionally equivalent), even though not structurally equivalent to the disclosed structure which performs the function in the herein illustrated embodiment or embodiments of the invention.

What is claimed is:

1. A method for correcting an optical response of an OCT interferometry system, the method comprising:
   characterizing the optical response of the OCT interferometry system, wherein characterizing the optical response comprises:
      generating electromagnetic radiation through a range of wavelengths based on an input signal, wherein each wavelength of generated electromagnetic radiation in the range of wavelengths corresponds to a portion of the input signal;
      splitting the electromagnetic radiation through a reference path and a sample path, wherein a sample does not lie in the sample path;
      for each wavelength of the range of wavelengths, detecting the electromagnetic radiation returned from the reference path and the sample path;
      generating an output signal corresponding to the received electromagnetic radiation and associated with each wavelength of the received electromagnetic radiation; and
      processing the output signals to determine for each wavelength in the range of wavelengths an optical loss of the OCT interferometry system;
   calculating a corrected input signal as a function of wavelength of electromagnetic radiation based on the determined optical loss, wherein for each wavelength of the range of wavelengths the corrected input signal is calculated by modifying the corresponding portion of the input signal based on the determined optical loss for the wavelength, such that when pre-emphasized electromagnetic radiation is split through the reference path and the sample path, the electromagnetic radiation returning from the reference path and the sample path does not contain periodic variations in intensity as a function of wavelength;

generating the pre-emphasized electromagnetic radiation based on the corrected input signal.

2. The method of claim 1, further comprising:
splitting the electromagnetic radiation through the reference path and the sample path, wherein the sample lies in the sample path;
detecting electromagnetic radiation returned from the reference path and the sample path, wherein the detector generates output signals corresponding to the received electromagnetic radiation; and
processing the output signals to generate an image.

3. The method of claim 1, wherein generating the electromagnetic radiation when characterizing the optical response comprises generating the electromagnetic radiation such that an intensity of the detected electromagnetic radiation is approximately constant across the range of wavelengths.

4. The method of claim 1, wherein:
a proxy reflector is inserted into the sample path such that electromagnetic radiation split through the sample path reflects off of the proxy reflector and generates a fringe signal, the fringe signal comprising electromagnetic radiation returning from the sample path; and
determining the optical loss comprises measuring an amplitude envelope of the output signal and calculating a correction signal from the amplitude envelope such that, when the generated electromagnetic radiation is pre-emphasized according to the correction signal and split through the reference path and the sample path, the detected electromagnetic radiation does not contain periodic variation in magnitude.

5. A system comprising:
an electromagnetic radiation source operable to generate electromagnetic radiation through a range of wavelengths based on an input signal, wherein each wavelength of the generated electromagnetic radiation in the range of wavelengths corresponds to a portion of the input signal;
an OCT interferometer coupled to the electromagnetic radiation source, wherein the OCT interferometer includes a reference path and a sample path;
a detector configured to:
receive electromagnetic radiation returned from the reference path and the sample path for each wavelength of the range of wavelengths; and
generate an output signal corresponding to the received electromagnetic radiation and associated with each wavelength of the received electromagnetic radiation; and
a controller coupled to the detector and the electromagnetic radiation source, wherein the controller:
selectively causes electromagnetic radiation to be generated through the range of wavelengths when a sample does not lie in the sample path;
processes the output signals to determine for each wavelength in the range of wavelengths an optical loss of the system; and
calculates a corrected input signal as a function of wavelength of electromagnetic radiation based on the determined optical loss, wherein for each wavelength of the range of wavelengths the corrected input signal is calculated by modifying the corresponding portion of the input signal based on the determined optical loss for the wavelength, such that the electromagnetic radiation returning from the reference path and the sample path does not contain periodic variations in intensity as a function of wavelength;
selectively causes pre-emphasized electromagnetic radiation to be generated based on the corrected input signal.

6. The system of claim 5, wherein selectively causing electromagnetic radiation to be generated when a sample does not lie in the sample path comprises selectively causing electromagnetic radiation to be generated having an intensity that is approximately constant across the range of wavelengths.

7. The system of claim 6, wherein the optical loss is compensated for using a correction proportional to the inverse of the output signals.

8. The system of claim 5, wherein the at least one electromagnetic radiation source is a semiconductor tunable laser source.

9. The system of claim 5, wherein the source comprises a semiconductor laser.

10. The system of claim 9, wherein the source is a sample grating distributed Bragg reflector (SG-DBR) laser.

* * * * *